United States Patent [19]

Wajaroff et al.

[11] Patent Number: 4,592,908
[45] Date of Patent: Jun. 3, 1986

[54] PROTECTIVE CREAM FOR THE SCALP AND METHOD OF STRAIGHTENING HAIR

[75] Inventors: Theodor Wajaroff, Darmstadt; Helga Gallist, Gross-Gerau, both of Fed. Rep. of Germany

[73] Assignee: Wella Aktiengesellschaft, Darmstadt, Fed. Rep. of Germany

[21] Appl. No.: 691,590

[22] Filed: Jan. 10, 1985

Related U.S. Application Data

[63] Continuation of Ser. No. 466,011, Feb. 14, 1983, abandoned.

[30] Foreign Application Priority Data

Feb. 20, 1982 [DE] Fed. Rep. of Germany ....... 3206204

[51] Int. Cl.$^4$ .......................... A61K 7/09; A61K 7/11; A61K 7/06; A45D 7/00
[52] U.S. Cl. ........................................ 424/71; 424/70; 424/72; 132/7
[58] Field of Search .................. 424/71, 72, 70; 132/7

[56] References Cited
PUBLICATIONS

Dr. H. Roempp, *Chemielexikon*, 5th Ed., p. 5385.

Primary Examiner—Albert T. Meyers
Assistant Examiner—F. Abramson
Attorney, Agent, or Firm—Michael J. Striker

[57] ABSTRACT

A cream is disclosed for protection of the scalp during hair straightening, composed of 10–80% by weight Vaseline®, and/or polyethylene dissolved in paraffin oil, 10–85% by weight of at least one oxethylated saturated or unsaturated $C_8$–$C_{18}$-fatty alcohol and/or oxethylated $C_6$–$C_{14}$-alkylphenol each with 2 up to 30 ethylene oxide units in the molecule, 0.5 up to 5.0% by weight of a physiologically compatible organic acid and/or a physiologically compatible, easily saponifiable ester of an organic acid, 0.001 up to 1.0% by weight of at least one pH-indicator and, if necessary, up to 1.0% by weight water as well as, if necessary, customary cosmetic additives. According to the likewise claimed method of straightening hair, the mentioned protective cream is applied to the scalp before the use of an alkaline hair straightening agent. If the alkaline hair straightening agent, subsequently applied to the hair, comes into contact with the protective cream, it is neutralized. In the event that a greater amount of straightening agent is not completely neutralized, this is shown by the color change of the indicator. Any unnoticeable injury to the scalp is precluded.

2 Claims, No Drawings

PROTECTIVE CREAM FOR THE SCALP AND METHOD OF STRAIGHTENING HAIR

This is a continuation of application Ser. No. 466,011, filed Feb. 14, 1983, now abandoned.

BACKGROUND OF THE INVENTION

The present invention concerns a cream for protection of the scalp before the action of alkaline hair straightening agents, as well as a method of straightening hair using this protective cream.

For the lasting straightening of human hair, strongly alkaline adjusted hair straightening agents have acquired a great significance. Most of these agents contain as alkalization agent and simultaneously effective straightening component, alkali hydroxide, particularly 2 up to 10% by weight sodium hydroxide. Through the use of this agent a relatively fast straightening without noteworthy negative alterations of the hair structure is possible.

For performance of a hair straightening, the hair straightening agent, which as a rule is provided in cream form or gel form, is uniformly distributed onto the hair. The increased viscosity of the hair straightening agent should avoid a running off from the hair and, on the other hand, with subsequent combing, resist the tendency of the hair to return to its original curled form. After the frequent combing necessary for smoothing of the hair during the processing time, which amounts to about 5 up to 20 minutes, the hair is carefully rinsed with water, in order to remove the hair straightening agent.

Although the hairdresser protects his hands by means of gloves, with the described hair straightening method, even with the greatest care, a contact of the alkaline straightening agent with the scalp of the customer cannot be completely avoided. Strongly alkaline straightening agents, in particular those based upon alkali hydroxides, cause skin irritations on the scalp as well as the appearance of burns, and with longer working-in periods they can even lead to etching of the scalp.

It is known, in order to avoid a contact of the hair straightening agent with the scalp, to apply a protective cream of Vaseline ® (a registered trademark representing petroleum jelly and being a mixture comprising hydrocarbon oils and paraffins with a melting range of 35°–45° C.) or water-containing gels, as well as oil-in-water- or water-in-oil-emulsions, thickly onto the hairy scalp as well as onto the forehead and the neck. During the working-in of the straightening agent on the hair it is, however, not possible to ascertain with these protective creams whether or not determined places on the scalp have nevertheless in risky manner come into contact with the hair straightening agents.

In other respects, protective creams composed of Vaseline ® have the disadvantage that they are very difficult to remove again after the straightening operation.

Aqueous emulsions or gels have no sufficient protective activity, since the alkali lye is able to penetrate these after a short time.

SUMMARY OF THE INVENTION

It is therefore an object according to the present invention to make available a protective cream and a method of straightening hair, which do not display the above-mentioned disadvantages.

It has been discovered that with a cream for protection of the scalp during hair straightening, composed of (A) 10 up to 87% by weight Vaseline ® and/or a solution of polyethylene in paraffin oil, (B) 10 up to 85% by weight of at least one oxethylated saturated or unsaturated $C_8$–$C_{18}$-fatty alcohol and/or oxethylated $C_6$–$C_{14}$-alkylphenol each with 2 up to 30 ethylene oxide units in the molecule, (C) 0.5 up to 5.0% by weight of a physiologically compatible organic acid and/or a physiologically compatible, easily saponifiable ester of an organic acid, (D) 0.001 up to 1.0% by weight of at least one pH-indicator and, if necessary, up to 1% by weight water as well as in given cases customary cosmetic additives, the stated object is attained in outstanding manner.

The solution of polyethylene in paraffin oil, usable alternatively to Vaseline ® for the cream according to the present invention, is obtained by heating the paraffin oil to about 120° C. and dissolving solid polyethylene, for example, polyethylene foil, therein.

As oxethylated fatty alcohol, there comes into consideration, for example, oxethylated oleyl alcohol with 2 up to 30 ethylene oxide groups, oxethylated cetylstearyl alcohol with 10 up to 30 ethylene oxide groups and oxethylated stearyl alcohol with 12 ethylene oxide groups. A suitable oxethylated alkylphenol is oxethylated p-nonylphenol, for example with 10 ethylene oxide groups.

Physiologically compatible organic acids, which are supposed to be contained in the described cream, include, for example, acetic acid, tartaric acid, adipic acid, ascorbic acid, succinic acid, glutamic acid, maleic acid, citric acid, benzoic acid, lactic acid, sorbic acid, glycolic acid, salicylic acid, fumaric acid and sulfosalicylic acid. The physiologically compatible acid can be replaced completely or partially also by physiologically compatible esters of organic acids. Examples of such esters include the glycerin ester of acetic acid, γ-butyrolactone and ethyleneglycol monostearate.

As pH-indicators there comes into consideration those which display a well visible color change in the pH-range between about 5 and 12. Particularly suitable pH-indicators include, for example, m-cresol purple, phenol red, neutral red, bromthymol blue, thymol blue, p-xylenol blue, o-cresolphthalein, phenolphthalein, p-xylenolphthalein, alizarin yellow GG, alizarin yellow R, β-naphtho violet and nitramine (N-methyl-N-2,4,6-tetranitroaniline).

The cream according to the present invention is preferably water-free; it can, however, without disadvantage, if necessary, contain up to 1% by weight water through the use of raw materials which are not completely water-free.

In other respects, the cream can moreover contain customary cosmetic additives, such as, for example, natural oils, such as olive oil, castor oil, peanut oil and avocado oil, moreover fatty alcohols, wool grease alcohol, fillers such as kaolin and colloidal silicic acid, silicone oil, care additives such as cholesterin, lanolin and lecithin, capillary-active compounds such as for example laurylpyridinium chloride, cationic non-capillary-active compounds such as for example diallyl-dimethylammonium chloride-homopolymerizate, as well as also allantoin, hamamelis extract, menthol Peruvian balsam, preservatives and perfume oils. Moreover, the cream can contain dyes, to the extent that the color change of the indicator is not thereby masked. With use of determined indicators, the use of determined dyes can also serve the purpose of improving the perceptibility of the color change or altering its color.

It has moreover been discovered that it is favorable, in case the protective cream is to be used with dark-skinned people, to add to this protective cream bright pigmenting substances, such as for example titanium dioxide, whereby the color change of the indicator is better recognized on a brighter background.

The use of the protective cream according to the present invention follows in the manner that one initially separates the hair into hanks and the protective cream according to the present invention is applied to the scalp as well as to the adjacent skin parts, for example the forehead and the neck, in uniform layers of about 1-2 mm thickness. In this connection care must be observed that the hair does not come into contact with the protective cream. Through the color of the employed indicator one is shown that the cream is adjusted neutral up to acid. Then the alkaline hair straightening agent, which preferably is provided as gel or cream, is applied to the hair, avoiding a contact with the scalp. During the work-in period of about 3 up to 20 minutes, preferably 3 up to 8 minutes, the hair is frequently combed through.

Small amounts of the alkaline hair straightening agent which may contact the parts of the scalp covered with the protective cream, during the combing or the application, are neutralized by the acid or the ester contained in the protective cream. In the event that greater amounts of the hair straightening agent contact the parts of the scalp covered with protective cream, they cannot be completely neutralized. The indicator shows in the corresponding places the alkalinity by means of color change. The hairdresser is therefore in a position, in order to avoid any injury to the scalp, to take countermeasures. In this case he can either additionally apply fresh protective cream to the places marked by color, until the indicator again shows neutral or acid reaction, or—in case this is not sufficient—he can remove the consumed protective cream from the places in consideration, for example with a spatula, and apply fresh protective cream.

After expiration of the working-in period, the hair straightening agent is carefully rinsed with water from the hair. Therewith one can also so proceed, towards the end of the rinsing of the hair, through massage against the scalp, to bring it into contact intensively with the residue of protective cream remaining on the scalp. In so doing, the alkaline straightening agent residue remaining in the hair can be neutralized. In the event that the indicator shows through its coloration towards the end of the rinsing, a still alkaline reaction, then a complete neutralization can be obtained through massaging the hair with an additional small amount of the protective cream and renewed rinsing out.

One can also proceed in a batchwise manner to perform the hair straightening as follows: After applying the protective cream, initially only a single hank of hair is treated with the hair straightening agent, combed frequently during a working-in period of about 3 up to 8 minutes, and subsequently the hank is carefully rinsed with water. These method steps are then performed on the next hank of hair, and so forth, until all of the hair hanks have been so treated.

During the hair straightening the scalp is outstandingly protected against the working-in of the alkaline hair straightening agent, and the hair will display natural lustre as well as a healthy appearance.

The novel features which are considered characteristic for the invention are set forth in particular in the appended claims. The invention itself, however, both as to its construction and its method of operation, together with additional objects and advantages thereof, will be best understood from the following description of specific embodiments.

DESCRIPTION OF THE PREFERRED EMBODIMENTS

EXAMPLE 1

| | |
|---|---|
| 76.75 g | vaseline ® |
| 21.00 g | oxethylated oleyl alcohol with 2-30 ethylene oxide groups |
| 2.20 g | lactic acid, 90% |
| 0.05 g | thymolphthalein |
| 100.00 g | |

If the neutralizing capacity of the above colorless protective cream is not sufficient, this will be indicated by a color change of the indicator (at pH 9.4-10.6) from colorless to blue.

EXAMPLE 2

| | |
|---|---|
| 86.47 g | vaseline ® |
| 10.00 g | oxethylated cetylstearyl alcohol with 30 ethylene oxide groups |
| 2.00 g | oxethylated p-nonylphenol with 10 ethylene oxide groups |
| 1.00 g | salicylic acid |
| 0.03 g | phenolphthalein |
| 0.50 g | perfume oil |
| 100.00 g | |

The indicator of this colorless protective cream shows, with pH 2.2-10.0 a color change from colorless to violet.

EXAMPLE 3

| | |
|---|---|
| 44.00 g | paraffin oil of density $\rho = 0.84$ g/cm$^3$ |
| 6.00 g | polyethylene (dissolved in the above 44 g paraffin oil) |
| 49.10 g | oxethylated cetylstearyl alcohol with 12 ethylene oxide groups |
| 0.85 g | benzoic acid |
| 0.05 g | thymol blue |
| 100.00 g | |

The indicator of this yellow-orange colored protective cream shows with a pH-value from 8.0-9.6, a color change from yellow/orange to blue.

All of the percentages given in the specification represent percentages by weight.

It will be understood that each of the elements described above, or two or more together, may also find a useful application in other types of physiological protection differing from the types described above.

While the invention has been illustrated and described as embodied in a protective cream for the scalp and a method of straightening hair, it is not intended to be limited to the details shown, since various modifications and structural changes may be made without departing in any way from the spirit of the present invention. p Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

We claim:

1. Method for straightening human hair, comprising the steps of applying to the scalp in uniform layers of about 1 to 2 mm thickness a cream for protection of the scalp during hair straightening, comprising
    (A) 10 to 87% by weight of petroleum jelly;
    (B) 10 to 85% by weight of oxyethylated $C_8$–$C_{18}$-fatty alcohol or an oxyethylated $C_6$–$C_{14}$-alkylphenol, each with from 2 up to 30 ethylene oxide units in the molecule;
    (C) 0.5 to 5.0% by weight of an organic acid or the easily saponifiable ester thereof selected from the group consisting of acetic acid, tartaric acid, adipic acid, ascorbic acid, succinic acid, glutamic acid, maleic acid, citric acid, benzoic acid, lactic acid, sorbic acid, glycolic acid, salicylic acid, fumaric acid and sulfosalicylic acid;
    (D) 0.001 to 1.0% by weight of a pH-indicator and
    (E) up to 1% by weight of water; then distributing an effective amount of a strongly alkaline hair straightening agent containing 2 to 10% by weight of alkali hydroxide uniformly onto the hair, combing the hair for a time period of about 3 to 20 minutes and thereafter rinsing the hair thoroughly with water.

2. The method according to claim 1, wherein the hair is separated into hanks before application of the strongly alkaline hair straightening agent containing 2 to 10% by weight of alkali hydroxide, and successively to each individual hank, initially said strongly alkaline agent of alkali hydroxide is applied, the hank is thereafter frequently combed through during a time period of about 3 up to 8 minutes, followed by thoroughly rinsing the hank with water.

* * * * *